United States Patent [19]

Yaszemski et al.

[11] Patent Number: 5,733,951
[45] Date of Patent: Mar. 31, 1998

[54] POLY(PROPYLENE FUMARATE)

[76] Inventors: Michael J. Yaszemski; Richard G. Payne, both of Lackland A.F.B., 59th Medical Wing/PSSB, 2200 Bergquist Dr., Ste. #1, San Antonio, Tex. 78236; Antonios G. Mikos, Rice University, 6100 Main St., Houston, Tex. 77005

[21] Appl. No.: 234,551

[22] Filed: Apr. 28, 1994

[51] Int. Cl.$^6$ .............................. C08G 63/02; C08K 3/32; A61F 2/00
[52] U.S. Cl. .................. 523/116; 523/114; 523/115; 424/78.31; 424/423; 424/549; 528/272
[58] Field of Search .................... 523/115, 116, 523/114; 424/78.31, 423, 549; 528/272

[56] References Cited

U.S. PATENT DOCUMENTS

| | | | |
|---|---|---|---|
| 4,243,763 | 1/1981 | Argentar | 523/116 |
| 4,722,948 | 2/1988 | Sanderson | 523/113 |
| 4,843,112 | 6/1989 | Gerhart et al. | 523/113 |
| 4,888,413 | 12/1989 | Domb | 528/272 |
| 5,286,763 | 2/1994 | Gerhart et al. | 523/113 |

OTHER PUBLICATIONS

Domb et al., *J. Polymer Science*, 28:973–985 (1990).
Gerhart et al., *J. Orthopedic Research*, 4:76–85 (1986).
Gerhart et al., *J. Orthopedic Research*, 6:585–592 (1988).
Gerhart et al., *J. Biomedical Materials Research*, 22:1071–1082 (1988).
Gerhart et al., *J. Biomedical Materials Research*, 23:1–16 (1989).
Goldstein, *Journal of Biomechanics*, 20:1055–1061 (1987).
Saha & Pal, *J. Biomedical Materials Research*, 18:435–462 (1984).

*Primary Examiner*—Andrew E. C. Merriam
*Attorney, Agent, or Firm*—Pravel, Hewitt, Kimball & Krieger

[57] ABSTRACT

A novel pathway for the synthesis of poly(propylene fumarate) includes first producing bis-hydroxypropyl fumarate and then its transesterification into poly(propylene fumarate). This synthetic pathway permits production of high molecular weight poly(propylene fumarate) and enables the production of a composite material useful in orthopedic procedures.

5 Claims, 2 Drawing Sheets

POLY(PROPYLENE FUMARATE)

BACKGROUND OF INVENTION

1. Field of the Invention

This invention relates to a novel method for the synthesis of poly(propylene fumarate), resulting high molecular weight forms of poly(propylene fumarate) with a relatively low poly dispersity index, and compositions useful in orthopedic applications.

2. Description of the Prior Art

Poly(propylene fumarate) is an unsaturated linear polyester which degrades in the presence of water into propylene glycol and fumaric acid, degradation products which are cleared from the human body by normal metabolic processes. Although poly(propylene fumarate) has been previously known, its routine, reproducible synthesis, and the synthesis of high molecular weight forms and forms within a narrow band of monodispersity of the polymer with low polydispersity index have not been previously accomplished. Known methods for the synthesis of poly(propylene fumarate), for example by equilibrium polycondensation, utilize reactions which are difficult to control. These synthetic methods typically require extremely high heat, the presence of a catalyst, and long reaction times. Premature crosslinking of the polymer often results, limiting the linear size or molecular weight of the linear polymer which can be achieved.

It would be highly desirable to provide an efficient, controlled synthetic reaction whereby poly(propylene fumarate) could be reproducibly synthesized, and high molecular weight linear poly(propylene fumarate) chains could be obtained.

SUMMARY OF THE INVENTION

The present invention solves the prior art problems of synthesis of poly(propylene fumarate) by providing a novel, efficient, quick and reproducible method for the synthesis of poly(propylene fumarate). In the synthetic method of the present invention, a two-step reaction process is used. First, the trimer bis(hydroxypropyl) fumarate is produced. In the second step, bis(hydroxypropyl) fumarate is transesterified to produce poly(propylene fumarate).

DESCRIPTION OF THE PREFERRED EMBODIMENT

Poly(propylene fumarate) is synthesized in a twostage reaction period. In the first stage, a fumaric acid derivative is combined with an excess of polypropylene glycol to yield bis-(hydroxypropyl) fumarate. This first step can be accomplished through several methods, some of which are described in FIGS. 1-4.

Figure 1:
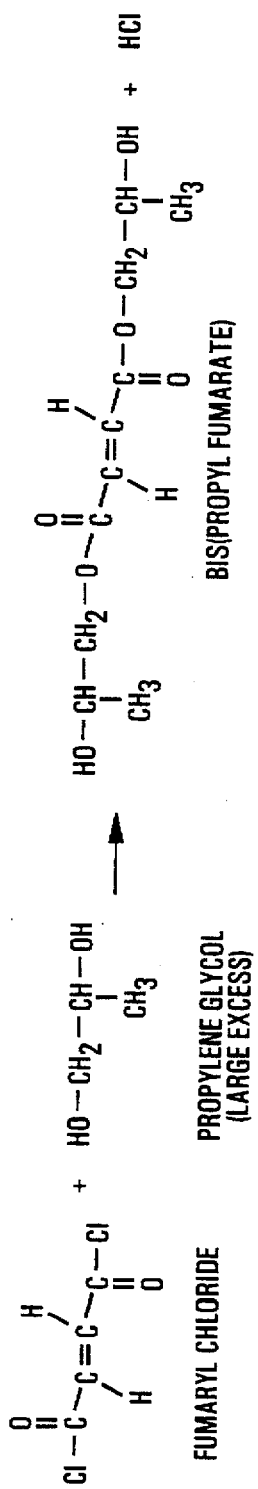
FIG. 1 shows the reaction pathway producing bis(hydroxypropyl) fumarate from fumaryl chloride.

The preferred method for producing bis-(hydroxypropyl) fumarate is to react fumaryl chloride with propylene glycol (PG). As shown in FIG. 1, fumaryl chloride is slowly added to approximately greater than two times molar excess propylene glycol generally at room temperature, in the absence of any catalyst. Hydrogen chloride gas given off by this reaction is captured and neutralized.

The reaction is exothermic. In general, it is desirable to maintain the temperature of the reaction below the boiling point of PG, e.g., below about 186° C. This is accomplished by controlling the rate of addition of fumaryl chloride.

Figure 2:
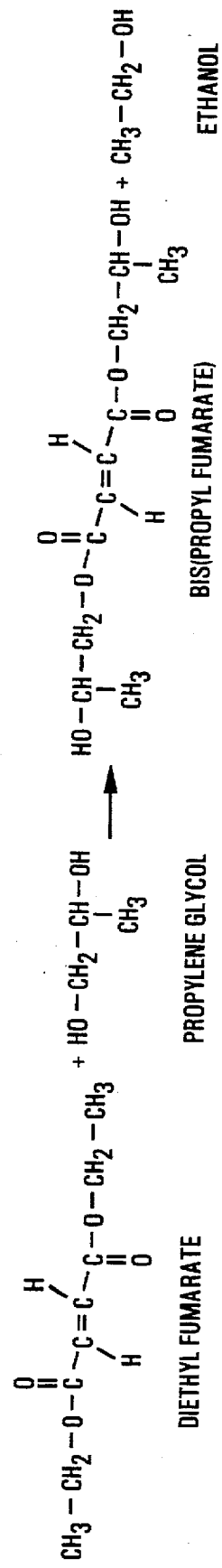
FIG. 2 shows the reaction pathway producing bis(hydroxypropyl) fumarate from diethyl fumarate.

An alternative method for producing bis-(hydroxypropyl) fumarate is shown in FIG. 2. Diethyl fumarate is reacted with approximately greater than two times molar excess of propylene glycol. The reaction is carried out at approximately 146° C. in the presence of an acid catalyst such as para-toluene sulfonic acid. Ethyl alcohol, a reaction product, is removed by condensation.

Figure 3:
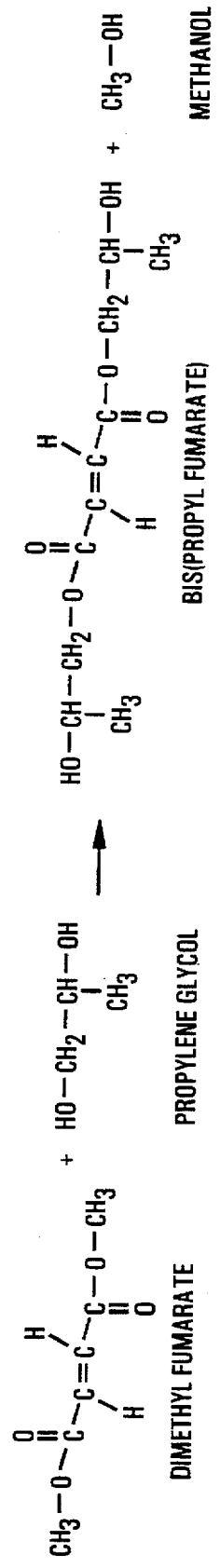
FIG. 3 shows the reaction pathway producing bis(hydroxypropyl) fumarate from dimethyl fumarate.
Figure 4:
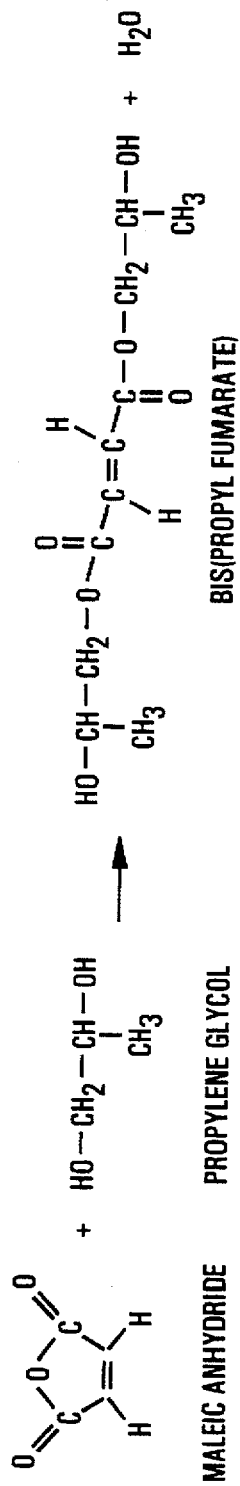
FIG. 4 shows the reaction pathway producing bis(hydroxypropyl) fumarate from maleic anhydride.

In a third alternative method for producing bis-(hydroxypropyl) fumarate, dimethyl fumarate is reacted with approximately greater than two times molar excess of propylene glycol. This reaction is also carried out at approximately 146° C. in the presence of an acid catalyst, such a para-toluene sulfonic acid. The reaction scheme is shown in FIG. 3. Methanol, a small molecule by-product of the reaction, is removed by condensation.

Yet another method of forming the bis-(hydroxypropyl) fumarate is to react maleic anhydride with approximately greater than two times molar excess of propylene glycol. The reaction is carried out in the presence of an acid catalyst such as para-toluene sulfonic acid at approximately 100° C. Water, the byproduct of this reaction is removed by condensation. The reaction sequence is displayed in FIG. 4.

In general, each of the above reaction methods which uses an acid catalyst should be maintained at a temperature above the boiling point of the small molecule byproduct given off in the reaction (e.g., ethyl alcohol, methanol, or water) but below approximately 180° C. in order to avoid increased side reactions.

In each of the above-described reactions, once bis-(hydroxypropyl) fumarate is formed, any acid catalyst is removed by solution-precipitation. The product is dissolved in THF, and the THF-solution is then dripped into approximately 6× volume of petroleum ether. Bis-(hydroxypropyl) fumarate precipitates out as a gummy, flowing precipitate, leaving the acid catalyst in the liquid phase which is poured off. The product is removed and dried, e.g., in a desiccator under vacuum to remove remaining solvents.

Figure 5:
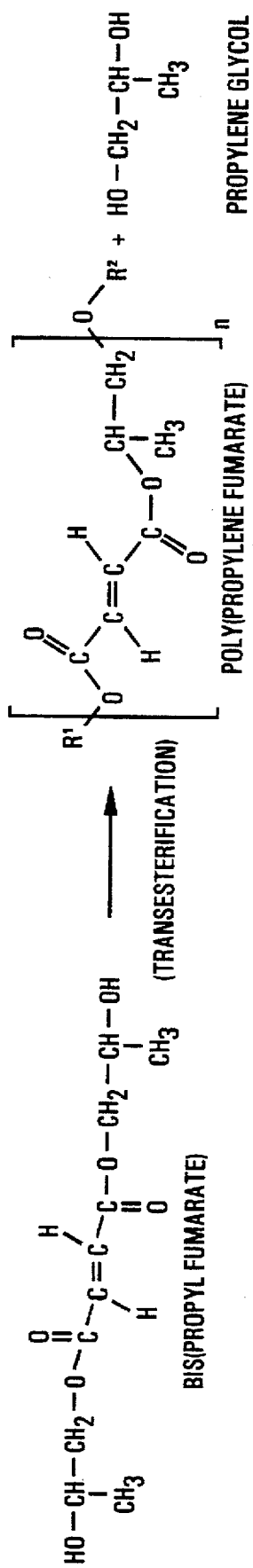
FIG. 5 shows the reaction pathway producing poly(propylene fumarate) from bis(hydroxypropyl fumarate).
Figure 5:
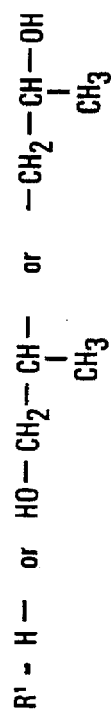
Figure 5:
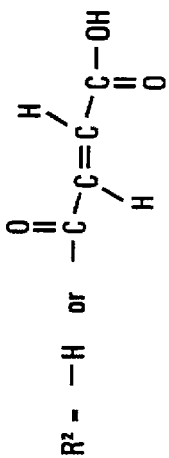

In the second step for the synthesis of poly(propylene fumarate) shown in FIG. 5, bis-(hydroxypropyl) fumarate is heated to approximately 160° C. under a vacuum of approximately 150 mm of mercury in the presence or absence of a basic catalyst such as antimony trioxide. Excess propylene glycol remaining from the first step is boiled off in this process, and bis-(hydroxypropyl) fumarate goes through a transesterification reaction yielding poly(propylene fumarate) product having a formula I as shown below. The poly(propylene fumarate) product is generally brown in color and translucent.

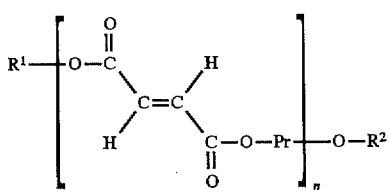

where

R1=H— or HO—Pr—

R2=—H or

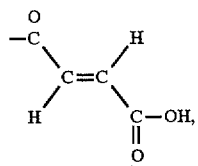

Pr = propyl group and n = approximately 2 to 15. Excess propylene glycol present during the reaction and produced as a product of the transesterification reaction is removed by condensation.

In this second step, the molecular weight of the resultant polymer may be further increased by increasing the reaction temperature and lowering the pressure. A suggested temperature range for the second step reaction is approximately 140° C. to approximately 220° C. It is preferred that the temperature be less than approximately 190° C. to avoid crosslinking. A suggested pressure range is approximately 30 mm of mercury to approximately 1 atmosphere. The viscosity of the resulting polymer product appears to be directly related to its molecular weight.

The polymer may be precipitated by dissolving in THF and dripping the THF solution into a 6×volume of petroleum ether. The resultant precipitate is removed, heated to approximately 110° C. for about 15 minutes, then dried, e.g., by placing in a vacuum desiccator at a pressure of approximately 1 mm of mercury overnight.

Although poly(propylene fumarate) is disclosed as a preferred polymer in the present invention, one of skill in the art will recognize other dicarboxylic acids and dialcohols which may be substituted for fumarate and propylene glycol in the instant invention. Suitable dicarboxylic acids include maleic acid, succinic acid, and the like which contain at least one double bond, and are biocompatible and biodegradable. Naturally occurring dialcohols which are non-toxic and which can be metabolized in the human body may be substituted for propylene glycol.

The preferred copolymers formed of fumarate and dialcohol form high molecular weight chains, e.g., of approximately 5-15 polymerization units, and are useful in forming bone cements with characteristics similar to that described for poly(propylene fumarate).

Poly(propylene fumarate) is useful as an orthopedic material, for example in the preparation of a composite for use as a bone cement. The higher molecular weight poly(propylene fumarate) of the present invention and its lower polydispersity index permits formulation of a bone cement of a higher compressive strength and modulus than previously possible with low molecular weight poly(propylene fumarate). Thus, the higher molecular weight poly(propylene fumarate) permits formulation of a bone cement having a compressive strength and modulus approximating that of normal human trabecular bone. This material has the further added advantage of being degradable in physiological fluids to products which are cleared from the human body by natural metabolic processes.

Normal human trabecular bone has an average compressive strength of approximately 5 MPa and modulus of approximately 50 MPa. See for example S. A. Goldstein, "The Mechanical Properties of Trabecular Bone: Dependence On Anatomic Location and Function" J. Biomechanics, 20:1055–1061 (1987). Conventional bone cements are formed of poly(methylmethacrylate) or poly(methylmethacrylate-co-styrene). The compressive strength of these bone cements is approximately 100 MPa. See, for example, S. Saha and S. Pal, "Mechanical Properties of Bone Cement: A Review" J. BiomedicalMaterials Research, 18:435–462 (1984). This is much higher than the mid-range for trabecular bone (5 MPa), and is of the same order or magnitude as the mid-range compressive strength for compact bone. The much greater compressive strength of prior art bone cements can lead to stress shielding and loss of adjacent bone. Other disadvantages of known bone cements include that they are not degradable, and continually accumulate fatigue damage as they are loaded, which sometimes leads to structural failure.

Particulate compositions containing poly(propylene fumarate) can be formulated for orthopedic applications. In general, such compositions consist of poly(propylene fumarate), a monomer capable of addition polymerization such as vinyl pyrrolidone, acrylic acid, methyl methacrylate, styrene, methacrylic acid, or 2hydroxy ethyl methacrylate, and copolymers thereof, an inorganic filler such as beta-tricalcium phosphate, sodium chloride or hydroxyapatite, a radical initiator such as benzoyl peroxide, azobisisobutyronitrile, or acetyl peroxide, and an accelerator such as N,N dimethyl toluidine. While it is preferred that the monomers used are biodegradable, it is contemplated that non-biodegradable monomers such as methyl methacrylate will form only short polymer chains, which, upon degradation of the poly(propylene fumarate) backbone, in vivo, will be cleared from a patient's body by normal metabolic processes. Various amounts of the specific ingredients may be combined to produce a useful product. For example, approximately equal amounts of the poly(propylene fumarate), monomer, and filler may be used. The amounts of each component may be varied according to the desired characteristics of the final composition, as known to one of skill in the art. Likewise, the amount of initiator and accelerator may be varied by one of skill in the art to produce a composite having desired physical characteristics. Preferably, the components are combined in a sterile field, and pass through a moldable putty stage prior to hardening. In addition, by varying the molecular weight of the poly(propylene fumarate) a composite material having desired strength and modulus characteristics, including that which approximates the physical characteristics of human trabecular bone, is produced.

EXAMPLE 1
FORMATION OF POLY(PROPYLENE FUMARATE) OF VARIED MOLECULAR WEIGHTS

1. PRODUCTION OF BIS(HYDROXYPROPYL) FUMARATE

Fumaryl chloride (FuCl) was distilled, yielding 195.5 g. Propylene glycol (PG), 489.4 g., was weighed out and placed in a 1000 L 3-neck flask. The FuCl was placed in a 500 ml separatory funnel and set in the center neck of the flask. A magnetic stir bar was placed in the PG. One neck of the flask was connected to a nitrogen tank and the other neck was connected to a tube whose opposite end was placed in the bottom of a 500 ml flask ¾ full of pyridine. The FuCl was dripped into the PG at such a rate so that addition was completed in 1.5 hours. Nitrogen was flowed through the reactor, removing evolved HCl gas, and carrying it to the pyridine where it was neutralized. The reaction system was initially begun at room temperature but grew warmer as the reaction progressed.

2. TRANSESTERIFICATION TO POLY(PROPYLENE FUMARATE)

A reactor consisting of a kettle having a 3 inlet port top was used to produce poly(propylene fumarate). One port provided nitrogen inlet, one access for a stirring rod, and the third was the gas exit port, leading to a side arm with a cold water condenser attached. The condenser fed into a graduated collection flask with a side port, allowing noncondensible gases to pass through a liquid nitrogen trap to the vacuum pump. Because the system was under partial vacuum, the reaction temperature was above the boiling point of the small molecules generated by the reaction, which travelled in the vapor phase through the outlet port to the condenser. There, these molecules condensed and collected in the graduated piece.

The reactor was placed in an oil bath heated to approximately 160° C. The product of step 1, 621.7 g. of bis (hydroxypropyl) fumarate, was added to the reactor and the nitrogen flow started. The nitrogen was preheated by passing through a 10 foot length of copper coil, 0.25 in O.D., which coil was immersed in the oil bath.

After ten minutes, antimony trioxide ($Sb_2O_3$), 10.9 g., was added, and the pressure was reduced to approximately 140 mm Hg. Condensation products were collected in the graduated portion following the condenser outlet.

After approximately seven hours, a sample was taken and its molecular weight was analyzed. The average Mn was 751 and Mw was 1310.

The pressure was reduced to about 70 mm Hg. and the temperature raised to about 180° C. After an additional hour, about eight reaction hours, the temperature was raised to about 200° C. and the pressure reduced to about 30 mm Hg. The reaction was stopped after an additional hour, approximately nine reaction hours. The final product had an average Mn of 849 and Mw of 1784. (Molecular weights were determined using gel permeation chromatography with polystyrene standards.)

The products were then purified by dissolving in tetrahydrafuran (THF) and centrifuging for approximately 15 minutes at approximately 3000 rpm. The supernatant was retrieved and the THF centrifugation process was repeated. Almost all of the catalyst was removed in this procedure.

EXAMPLE 2

TRANSESTERIFICATION IN THE ABSENCE OF CATALYST

Poly(propylene fumarate) was prepared as described in Example 1 except in the absence of catalyst. The reaction was terminated after 30 hours and molecular weight of the poly(propylene fumarate) product was determined as described for Example 1.

| Mn | Mw | MWD |
|------|------|------|
| 1224 | 1904 | 1.56 |

EXAMPLE 3

SYNTHESIS OF A PARTICULATE COMPOSITE MATERIAL
CONTAINING VARIOUS MOLECULAR WEIGHT POLY(PROPYLENE FUMARATE)

Three variations of a particulate composite material were formulated. The recipe for the composite was the same in all three groups with the exception of the prepolymer's molecular weight. The formulation consisted of equal parts by weight of poly(propylene fumarate), tricalcium phosphate, and vinylpyrrolidone.

Poly(propylene fumarate) was produced essentially as described for Example 1, except that the trimer, bis-(hydroxy propyl) fumarate was produced from diethyl fumarate using an acid catalyst by the following methods.

Diethyl fumarate (DEF) and propylene glycol (PG) were distilled. PG, 539.3 g., was combined with 246.9 g. DEF in the reaction kettle and heated to 140° C. Para Toluene Sulfonic Acid (pTSA), 13.7 g. was added to the heated mixture as an acid catalyst. Condensate (primarily ethanol with a little PG) was collected throughout the course of the reaction which was run for 8.5 hours at 140° C. The reaction mixture was then cooled and placed in 400 mL petroleum ether, stirring overnight in order to remove the pTSA, which is soluble in petroleum ether, in contrast to the reaction products.

The petroleum ether was decanted, and the product was heated to 195° C. After stirring for 15 minutes (to ensure all of the petroleum ether was driven off) 13.0 g. antimony (III) oxide ($Sb_2O_3$) was added. Samples were taken at one hour, two hours, and 3.5 hours after addition of the antimony (III) oxide, and the reaction was ended after 3.5 hours. The trimer product was then reacted as described for Example 1 to produce poly(propylene fumarate) of differing average molecular weights for use in preparing composites.

Benzoyl peroxide, an initiator for the radical polymerization of vinylpyrrolidone and the unsaturated carbon-carbon bonds on the poly(propylene fumarate), was added in an amount of one mole percent based on the amount of vinylpyrrolidone. N,N-dimethyltoluidine (DMT) was added as an accelerator to allow the spontaneous decomposition of benzoyl peroxide into radicals to occur at an appropriate rate at room temperature. An appropriate rate was defined as one that would permit the composite to harden in approximately 10 to 15 minutes. This was accomplished by using 4.8 microliters of DMT.

The composite material was packed into Teflon molds while it was still in a viscous state prior to hardening. The molds were right circular cylinders, 6 mm diameter by 12 mm height. These molds produced pellets for mechanical testing that were in accordance with the specifications for testing bone cements via ASTM F451-86. Ten pellets were made from each molecular weight formulation. These were allowed to remain in the molds overnight, and were then pressed out of the molds to undergo compressive testing. The tests were performed to failure on an Instron 1125 electromechanical materials testing machine, and the compressive strength and modulus were recorded for each specimen in accordance with the ASTM F451-86 standard for acrylic bone cements.

The mechanical tests were performed as follows. The Instron was fitted with a 5 kiloNewton reversible load cell. The load cell and machine base had flat platens installed for compression testing. The gage length was set at 12.2 mm, and mechanical safety stops appropriate for this configuration were set in place. Zero, balance, and electronic calibration of the load measuring system were performed. The computer control and data acquisition system were programmed for testing to failure in compression at a crosshead speed of 1 mm per minute, in accordance with ASTM 451-86. The load versus deformation curve was recorded continuously until failure, and the ultimate compressive strength and elastic modulus were calculated from the data for each specimen.

The number average molecular weights (Mn) for the three groups of prepolymer used to produce the composites were 507, 938, and 2,038. The corresponding weight average molecular weights (Mw) were 658, 1694, and 11,916, respectively. The compressive strengths and compressive moduli of composites made from these three molecular weights of prepolymer (poly-propylene fumarate) appear in Table 1 (n=10). Each prepolymer made a composite that passed through a viscous putty stage suitable for molding as required in its intended orthopedic application. The third group ($M_n$2,038, $M_w$=11,916) did not go into solution in the vinylpyrrolidone monomer as quickly or as thoroughly as did the other two molecular weight groups.

TABLE I

|  | GROUP 1 | GROUP 2 | GROUP 3 |
|---|---|---|---|
| Mn | 507 | 938 | 2,038 |
| Mw | 658 | 1694 | 11,916 |
| MWD | 1.30 | 1.81 | 5.85 |
| Strength, MPa | 2.38 | 8.48 | 6.06 |
| Modulus, MPa | 12.2 | 45.4 | 42.3 |

The compressive strength and modulus of the composite increased with increased molecular weight of the polymer from Group 1 to Group 2. We anticipated a similar increase from Group 2 to Group 3, but it did not occur. We postulate as a reason why this may not have occurred, that some crosslinking of the poly(propylene fumarate) double bonds in the Group 3 prepolymer may have formed. The Group 3 prepolymer was slower to dissolve in vinylpyrrolidone monomer than the other two groups. Also, a product that resulted from taking the reaction just slightly further (i.e. application of 10 mm Hg. vacuum) was insoluble in tetrahydrofuran and two stronger solvents.

Additional composites have been formed using poly (propylene fumarate) of molecular weights between that of Group 1 and Group 3 above and having a MWD of approximately 1.8 to 2.2. These have been tested for compressive strength and modulus according to the methods described.

Tests indicated a linear relationship exists between molecular weight of the polymer and the compressive strength and modulus of the resulting composite up to approximately 15,000 Mw/1000 Mn. Thereafter, further increase in molecular weight did not induce further increase in compressive strength or modulus.

Having described the invention above, various modifications of the techniques, procedures, material and equipment will be apparent to those in the art. It is intended that all such variations within the scope and spirit of the appended claims be embraced thereby.

What is claimed is:

1. A method for the synthesis of poly(propylene fumarate) comprising the steps of:

reacting a monomer composition consisting essentially of bis(hydroxypropyl) fumarate under conditions sufficient to cause its transesterification; and recovering a compound having the formula:

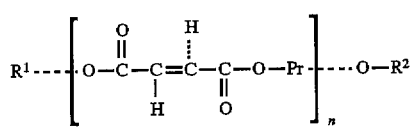

where R1 is H— or HO—Pr—
   $R^2$ is —H or —C(O)—CH=CH—C(O)OH
   Pr is propyl or isopropyl, and
   n is approximately greater than 2.

2. The method of claim 1, wherein n is from about 5 to about 15.

3. The method of claim 1, wherein Pr is isopropyl.

4. A method for the synthesis of high molecular weight poly(propylenefumarate) comprising the steps of:

reacting a monomer composition consisting essentially of bis(hydroxypropyl) fumarate under heat and vacuum conditions sufficient to cause its transesterification; and recovering poly(propylenefumarate) having a weight average molecular weight of at least 1500 and a polydispersity index of less than 2.2.

5. The method of claim 4, wherein said heat is less than 220° C.

* * * * *